(12) United States Patent
Davis et al.

(10) Patent No.: US 6,186,144 B1
(45) Date of Patent: Feb. 13, 2001

(54) TRANSPONDER INSERTION DEVICE AND METHOD

(75) Inventors: Langdon Davis, Augusta, GA (US); R. Michael Buffum, West Hills, CA (US); Garyld Harms, Woodbury; Doyle L. Cameron, Minneapolis, both of MN (US)

(73) Assignee: TraceNet Technologies, Inc., Burnsville, MN (US)

( * ) Notice: Under 35 U.S.C. 154(b), the term of this patent shall be extended for 0 days.

(21) Appl. No.: 09/257,568

(22) Filed: Feb. 25, 1999

Related U.S. Application Data

(60) Provisional application No. 60/075,860, filed on Feb. 25, 1998.

(51) Int. Cl.[7] .................................................. A61B 19/00
(52) U.S. Cl. .......................................... 128/897; 128/899
(58) Field of Search .................................... 128/897–899; 119/174

(56) References Cited

U.S. PATENT DOCUMENTS

| | | |
|---|---|---|
| 3,313,301 | 4/1967 | Jefferts . |
| 3,820,545 | 6/1974 | Jefferts . |
| 4,909,250 | 3/1990 | Smith . |
| 5,193,540 | 3/1993 | Schulman et al. . |
| 5,211,129 | 5/1993 | Taylor et al. . |
| 5,482,008 | 1/1996 | Stafford et al. . |

*Primary Examiner*—John P. Lacyk
(74) *Attorney, Agent, or Firm*—Patterson, Thuente, Skaar & Christensen, P.A.

(57) ABSTRACT

A system for simply and effectively introducing transponders into human or animal recipients is disclosed. A transponder, such as a microchip, is coated with a degradable coating and shaped so that is may be pushed through the recipient's skin. An insertion tool is used as indicated by the type of recipient. The tool receives the transponder, protects the transponder while it is pushed into the skin, and releases the transponder when rotated.

33 Claims, 2 Drawing Sheets

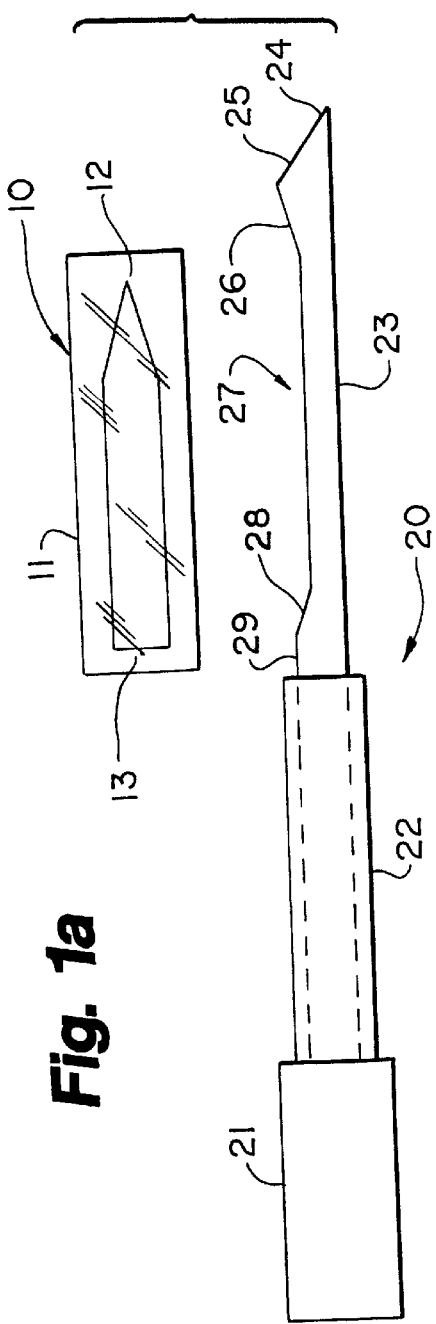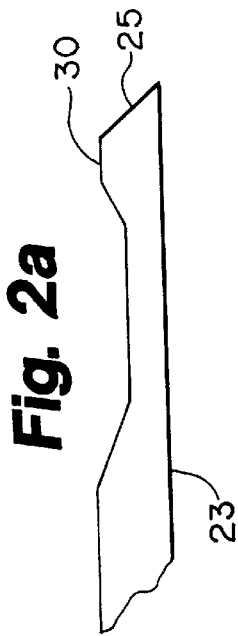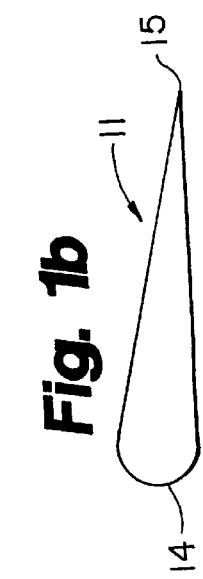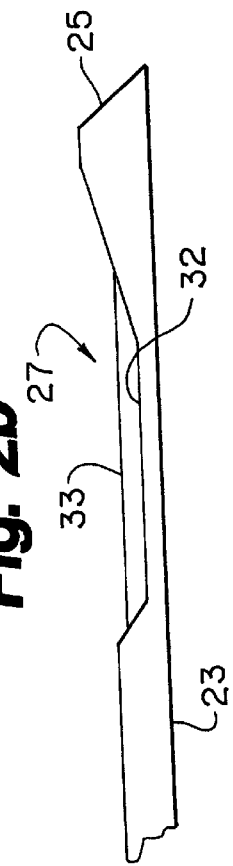
Fig. 1a
Fig. 1b
Fig. 2a
Fig. 2b

TRANSPONDER INSERTION DEVICE AND METHOD

RELATED APPLICATION

This application claims the benefit of U.S. Provisional Application No. 60/075,860, filed Feb. 25, 1998.

BACKGROUND OF THE INVENTION

1. Field of the Invention

The invention relates to human and animal location, identification, and retrieval systems, and particularly to systems of transponder insertion.

2. Background

Transponders implanted within a human or animal recipient have many uses. For instance, transponders are useful for tracking and monitoring animals and for managing recipient information. For instance, the position and identity of animals may be tracked with an implanted transponder. Convenient, inexpensive, sterile, and efficient implantation techniques, however, are needed. Such techniques, for instance, can include surgical procedures or syringe-based injection.

The present invention sets forth a system for simple and effective introduction of a transponder into a recipient. In some embodiments the system requires use of an insertion tool. The tool has a recessed opening with a shape configured for use with the transponder unit described herein, and is used in combination with a rotational step.

SUMMARY OF THE INVENTION

A system for implanting a transponder is described. The system allows the transponder to be manually pushed through the skin into an animal recipient. The system includes an insertion tool that is helpful for recipients that have resilient skin. The transponder is preferably a chip-type transponder.

In the first embodiment, a coated transponder is made by substantially covering a transponder with a degradable coating. The coated transponder unit is made with a sharp end and a blunt end. The sharp end of the unit is placed against the skin and the user pushes on the blunt end to force the unit through. The unit's sharpness may be derived from the coating or from the transponder. The stiffness of the unit may be provided by either the transponder or the coating. The unit preferably has a bullet-shape but may have a variety of shapes; for instance, a beveled sharp end and a rounded blunt end.

The coating is made of a degradable material. The material is preferably a water-soluble starch but may also be a simple sugar or protein coating. Natural or synthetic, biodegradable, and hydrolytically degradable materials may be used. The coating may be soft or could be stiff. A stiff coating may be made rigid so that it deforms slightly upon impact so that the transponder is shielded from blows or forces applied to the unit during implantation. The coating may include therapeutic agents, for instance, antibiotics.

The unit is sterilely packaged. The packaging should be easily opened by the user and the sterile inside surface of the package may be configured to provide a surface useful for gripping the unit. Thus a user may open the package and, without directly touching the unit, push it into the recipient.

The system allows for quick, sterile, and simple insertion of the transponder. The procedure can be performed after little or no training. In most cases the transponder unit is pushed directly into the recipient; the optimal place is usually the loose skin located between the shoulder blades in the direct midline of the back. The skin may be grasped between thumb and forefinger and pulled up into a "tent." The transponder unit is pushed directly through the skin until it disappears. In animals with resilient skin, such as dogs and cats, the insertion tool may be needed.

In another embodiment, the system includes an insertion tool. This tool comprises a handle attached to a rod-shaped cylinder that has a receptacle for receiving the transponder unit. A sleeve fits over the cylinder and reversibly slides over the cylinder and over the transponder in the receptacle. The transponder unit is placed in the receptacle of the tool with its sharp end forward, the sleeve is pushed over it, and the cylinder is pushed through the skin. The sleeve is pulled down so that the transponder is exposed. The cylinder is then rotated so that the transponder separates from the receptacle. The insertion tool is removed and the transponder is left behind under the skin. Prior to its use, the insertion tool should be sterilized by autoclave, sterilizing solution, or other suitable means. Care should be taken not to blunt the sharp end of the tool.

The shape of the cylinder and receptacle are designed to minimize trauma to tissue upon insertion and removal. Further, the receptacle may be coated with a low-tack material that gently holds the transponder unit in place until the rotation step. The tool may be weighted for optimal comfort by, for instance, adjusting the size of the handle. The tool may be rotated by twisting the handle or by incorporating an optional rotatable joint. Other joints may be introduced to the device to enhance deposition of the transponder; for instance, a flex-joint could be introduced below the receptacle so that the cylinder could be bent after pulling back the sleeve.

These embodiments are for illustrative purposes and are not intended to limit the scope of the invention. This invention encompasses many other embodiments that will be obvious to one skilled in these arts after reading this disclosure.

BRIEF DESCRIPTION OF THE DRAWINGS

FIG. 1a is a side elevational view depicting the transponder introduction system, including a coated transponder unit in a sterile package and an insertion tool;

FIG. 1b is a side elevational view depicting an alternative configuration of the coated transponder unit;

FIG. 2a is a fragmentary, side elevational view depicting an alternative configuration of the insertion end of the insertion tool;

FIG. 2b is a fragmentary, side elevational view depicting another alternative embodiment of the cylindrical part of the insertion tool.

DETAILED DESCRIPTION OF THE DRAWINGS

Figure 3:
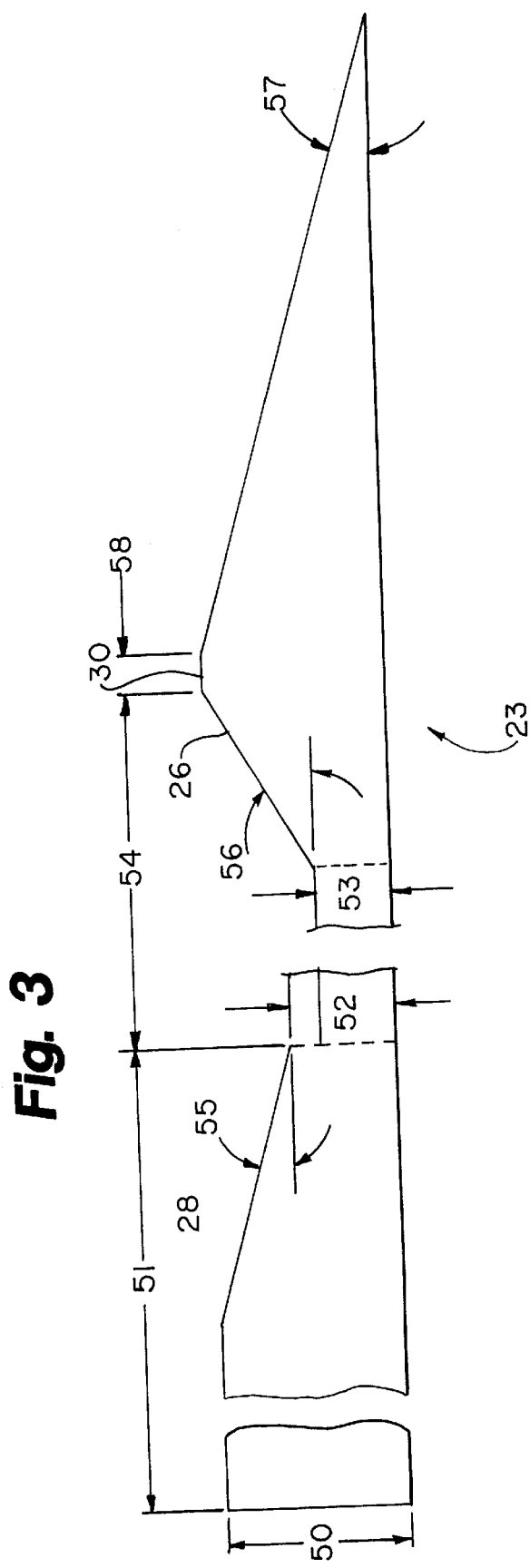
FIG. 3 is an enlarged, fragmentary, side elevational view depicting the insertion end.

FIG. 1a shows coated transponder unit 10 with sharp pointed end 12 and opposing flat blunt end 13. Coated transponder unit 10 may be grasped by the user with pointed end 12 resting on the recipient's skin and pushed at blunt end 13 through the skin of the recipient. The unit 10 is depicted in FIG. 1a packaged in a sterile package. The degradable capsule will protect the transponder during implantation, but later erode to maximize transponder function. The transponder unit is delivered to the user in sterile packaging (not shown) that optionally may be configured to be helpful for sterile gripping of the transponder unit.

Insertion tool 20 comprises handle 21, sliding sleeve 22, and cylinder 23. Cylinder 23 includes a sharp end 24, a front slope 25, a back slope 26, a receptacle 27 for the transponder unit, a rear slope 28, and a diameter 29. Transponder unit 10 or 12 is inserted into receptacle 27 and sliding sleeve 22 slides forward to cover receptacle 27. Insertion tool 20 is pushed through a recipient's skin and sleeve 22 is moved back to uncover receptacle 27. The user grips handle 21 and rotates the insertion tool so that the transponder unit is separated. The tool is withdrawn.

The shape of the cylinder may be varied; front slope 25, back slope 26, rear slope 28, and diameter 29 may be resized or adjusted to achieve a wide variety of shapes. Adjusting these parameters is helpful for achieving a tool with optimum characteristics for minimizing trauma and perfecting separation of the transponder unit form the cylinder. Other joints, locks, and features described above may also be incorporated.

FIG. 2a shows another embodiment of the shape of cylinder; in this embodiment, front slope 25 differs from that of FIG. 1 and a flat portion 30 is introduced. FIG. 2b shows another slope for front slope 25 and demonstrates how receptacle 27 may have first side wall 33 and second side wall 32 with varying heights. This feature is potentially useful for enhancing separation of the transponder unit from the receptacle.

FIG. 3 shows a particular embodiment of the cylinder 23. Cylinder diameter 50 is 0.148 inches. Length 51 is 3.5 inches. Angle 55 for the rear slope 28 is 16 degrees. Receptacle opening rear height 52 is 0.0855 inches and receptacle opening forward height 53 is 0.0625 inches. The distance 54 from receptacle opening rear height 52 to flat portion 30 is 1.11 inches. Flat portion 30 width is 0.03125 inches. The angle 56 for back slope 26 is 30 degrees. The angle 57 for the sharp end is 16 degrees.

What is claimed is:

1. An implantable transponder system adapted for implantation within a recipient, the implantable transponder system comprising:
   a transponder;
   a degradable capsule that substantially covers the transponder;
   a first portion comprising a sharp tip whereby the skin of the recipient may be penetrated; and
   a second portion comprising a surface adapted for being pushed.

2. The system of claim 1 wherein the transponder is a microchip transponder.

3. The system of claim 2 wherein the degradable capsule incorporates the sharp tip of the first portion, wherein the degradable capsule is sharp and rigid.

4. The system of claim 2 wherein the transponder includes a transponder case incorporating the sharp tip of the first portion.

5. The system of claim 2 wherein the degradable capsule includes the second portion.

6. The system of claim 5 wherein the second portion is a flat surface.

7. The system of claim 5 wherein the second portion is a concave surface.

8. The system of claim 6 wherein the first and the second portions are substantially opposite each other, whereby the sharp tip is adapted for placement against the skin of the recipient and penetrate the skin as a result of force applied directly to the flat surface.

9. The system of claim 4 wherein the first and the second portions are substantially opposite each other, whereby the sharp tip is adapted for placement against the skin of the recipient and penetrate the skin as a result of force applied directly to the flat surface.

10. The system of claim 1 wherein the degradable capsule comprises a starch based compound.

11. The system of claim 1 wherein the degradable capsule comprises a water-soluble degradable material.

12. The system of claim 1 wherein the degradable capsule comprises a sugar compound.

13. The system of claim 1 wherein the system includes sterile packaging, the packaging adapted for use in sterilely grasping the encapsulated transponder.

14. The system of claim 13 wherein the sterile packaging includes a wrapper with a sterile inner surface adapted to touch the encapsulated transponder.

15. An implantable transponder system adapted for implantation within a recipient, the implantable encapsulated transponder system comprising:
   an encapsulated transponder comprising a microchip transponder substantially encased within a degradable capsule that substantially covers the transponder, wherein the encapsulated transponder has a first end that is sharp and a substantially flat second end opposed from the first end.

16. The system of claim 15 wherein the degradable capsule has a rigid outer structure that prevents the process of pushing the transponder system through the skin from communicating forces to the transponder inside the capsule, whereby the capsule is protected from the forces generated by implantation.

17. A tool for implanting an implantable transponder within a recipient, the tool comprising:
   a handle;
   a delivery cylinder operably coupled to the handle;
   a cylinder including a receptacle adapted to receive the transponder; and
   a sliding sleeve shiftably received by the cylinder,
   the sliding sleeve shiftable across the cylinder while the transponder is in the receptacle.

18. The tool of claim 17 wherein the cylinder comprises a sharp end whereby the cylinder is adapted to be pushed through the skin of the recipient.

19. The tool of claim 18 wherein the receptacle means comprises an opening.

20. The tool of claim 19 wherein the opening has beveled edges.

21. The tool of claim 19 wherein the opening comprises a first edge parallel to a first plane and a second edge parallel to a second plane, wherein the first edge is closer to the sharp end than the second edge and the first plane forms an angle between 0 and 85 degrees that is perpendicular to the longitudinal central axis of the cylinder, and the second plane forms an angle between 0 and 85 degrees with the reference plane.

22. The tool of claim 21 wherein the first plane defines an angle of approximately 60 degrees from the reference plane and the second plane defines an angle of approximately 74 degrees from the reference plane.

23. The tool of claim 19 wherein the opening comprises a shape that only partially conforms to the shape of the transponder whereby the transponder is adapted to be easily separated from the opening after insertion of the cylinder beneath the skin.

24. The tool of claim 19 wherein the opening comprises a shape that minimizes trauma to the skin during insertion and removal from the recipient.

25. The tool of claim 19 wherein the sliding sleeve comprises a lip whereby the sliding sleeve is adapted to be easily manipulated by a user.

26. The tool of claim 19 wherein the receptacle is coated with a substance that enhances the sticking of the encapsulated transponder.

27. An implantable transponder system adapted for implantation within a recipient, the implantable transponder system comprising:

a transponder;

a degradable capsule substantially covering the transponder;

a tool for implanting the transponder, the tool comprising:
  a handle, a delivery cylinder, and a sliding sleeve, wherein:
    the delivery cylinder is attached to the handle and the cylinder comprises a receptacle means to receive the transponder,
    the sliding sleeve fits over the cylinder and is configured to slide back and forth across the cylinder, and
    wherein the sliding sleeve slides back and forth across the cylinder while the degradable capsule is in the receptacle means.

28. The system of claim 27 wherein the cylinder of the tool comprises a sharp end whereby the cylinder is adapted to be pushed through the skin of the recipient.

29. The system of claim 27 wherein the receptacle means comprises an opening.

30. The system of claim 29 comprising sterile packaging adapted for sterilely gripping the transponder after the transponder has been removed from the packaging.

31. The system of claim 27 wherein the degradable capsule comprises at east one antibiotic.

32. A method of implanting transponders within a recipient, the method comprising the steps of:

providing a transponder with a degradable coating, wherein the transponder is sterile, is substantially coated by the degradable coating, and comprises a sharp edge; and manually pushing the transponder through the skin of the recipient.

33. A method of implanting transponders within a recipient, the method comprising the steps of:

providing a transponder with a degradable coating, wherein the transponder is sterile, is substantially coated by the degradable coating, and comprises a sharp edge;

providing an insertion tool, the tool comprising:
  a handle, a delivery cylinder, and a sliding sleeve, wherein-
    the delivery cylinder is attached to the handle and the cylinder comprises a receptacle means to receive the transponder; and
    the sliding sleeve fits over the cylinder and is configured to slide back and forth across the cylinder;
  inserting the coated transponder into the receptacle means;
  pushing the sleeve over the receptacle means whereby the coated transponder is covered;
  manually pushing the insertion tool through the skin of the recipient;
  sliding the sleeve back to reveal the coated transponder;
  rotating the insertion tool at least 180 degrees and separating the transponder from the tool; and
  removing the insertion tool.

\* \* \* \* \*